(12) United States Patent
Stoilos et al.

(10) Patent No.: US 11,113,300 B2
(45) Date of Patent: Sep. 7, 2021

(54) SYSTEM AND METHOD FOR ENABLING INTEROPERABILITY BETWEEN A FIRST KNOWLEDGE BASE AND A SECOND KNOWLEDGE BASE

(71) Applicant: Babylon Partners Limited, London (GB)

(72) Inventors: Georgios Stoilos, London (GB); David Geleta, London (GB); Damir Juric, London (GB); Gregory McKay, London (GB); Jonathan Moore, London (GB); Jessica Tanon, London (GB); Claudia Schulz, London (GB); Mohammad Khodadadi, London (GB)

(73) Assignee: Babylon Partners Limited, London (GB)

(*) Notice: Subject to any disclaimer, the term of this patent is extended or adjusted under 35 U.S.C. 154(b) by 0 days.

(21) Appl. No.: 16/425,224

(22) Filed: May 29, 2019

(65) Prior Publication Data

US 2020/0380005 A1 Dec. 3, 2020

(51) Int. Cl.
*G06F 16/25* (2019.01)
*G06F 16/28* (2019.01)
(Continued)

(52) U.S. Cl.
CPC .......... *G06F 16/25* (2019.01); *G06F 16/2282* (2019.01); *G06F 16/248* (2019.01);
(Continued)

(58) Field of Classification Search
CPC ........ G06F 16/27; G06F 16/25; G06F 16/284; G06F 16/367; G06F 16/9024;
(Continued)

(56) References Cited

U.S. PATENT DOCUMENTS 10,038,611 B1 7/2018 Wu
10,602,215 B1 3/2020 Matthews
(Continued)

OTHER PUBLICATIONS

Madhavan et al., "Generic Schema Matching with Cupid," Microsoft Technical Report MSR-TR-2001-58, Aug. 2001 (Year: 2001).*
(Continued)

*Primary Examiner* — Ann J Lo
*Assistant Examiner* — Scott R Gardner
(74) *Attorney, Agent, or Firm* — McDermott Will & Emery LLP

(57) ABSTRACT

The subject-matter described herein relates to a computer-implemented method of enabling interoperability between a first knowledge base and a second knowledge base. Each knowledge base is graphically represented and includes a plurality of nodes each defining a concept and a plurality of relations linking the plurality of nodes. The first knowledge base and the second knowledge base are encoded using different coding standards. The method comprises: identifying an entity from the plurality of entities in the second knowledge base; obtaining a mapping between the identified entity from the second knowledge base and a matching entity from the first knowledge base; and creating and storing a link between the identified entity from the second knowledge base and the matching entity from the first knowledge base.

8 Claims, 11 Drawing Sheets

(51) Int. Cl.

| | | |
|---|---|---|
| *G06N 5/04* | (2006.01) | |
| *G06N 5/02* | (2006.01) | |
| *G06F 40/295* | (2020.01) | |
| *G16H 50/70* | (2018.01) | |
| *G06F 16/27* | (2019.01) | |
| *G06F 16/22* | (2019.01) | |
| *G06F 16/2457* | (2019.01) | |
| *G06F 16/248* | (2019.01) | |
| *G06F 40/279* | (2020.01) | |
| *G06N 20/00* | (2019.01) | |

(52) U.S. Cl.
CPC ........ *G06F 16/24578* (2019.01); *G06F 16/27* (2019.01); *G06F 16/284* (2019.01); *G06F 16/288* (2019.01); *G06F 40/279* (2020.01); *G06F 40/295* (2020.01); *G06N 5/022* (2013.01); *G06N 5/04* (2013.01); *G16H 50/70* (2018.01); *G06N 20/00* (2019.01)

(58) Field of Classification Search
CPC ...... G06F 17/2785; G06N 5/022; G06N 5/04; G06N 20/00; G06N 5/02
See application file for complete search history.

(56) References Cited

U.S. PATENT DOCUMENTS

| | | |
|---|---|---|
| 2005/0256850 A1 | 11/2005 | Ma |
| 2006/0218158 A1 | 9/2006 | Stuhec |
| 2013/0254184 A1 | 9/2013 | Ellsworth et al. |
| 2017/0286495 A1 | 10/2017 | Ott |

OTHER PUBLICATIONS

Dhamankar et al., "iMAP: Discovering Complex Semantic Matches between Database Schemas," SIGMOD 2004, Jun. 13-18, 2004, Paris, France (Year: 2004).*
Boukottaya et al, "Schema Matching for Transforming Structured Documents," DocEng '05, Nov. 2-4, 2005, Bristol, United Kingdom (Year: 2005).*
Scheide, A., "Interoperability Matters: Teh ONC Interoperability Roadmap and Standards Advisory", Inside Angle, Feb. 11, 2015, 3 pages.
Lau, M., Mapping between the code systems of different countries: A case study—CCI to ICD-10-PCS, Aug. 2, 2017, 2 pages.
Shaviko, P., et al., "Ontology matching: state of the art and future challenges", IEEE Transactions on Knowledge and Data Engineering, Institute of Electrical and Electronics Engineers, 2013, 25 (1), pp. 158-176. <10.1109/TKDE.2011.253>. <hal-00917910>.
Bodenreider, O., "The Unified Medical Language System (UMLS): integrating biomedical technology", Nucleic Acids Research, 2004, vol. 32, Database issue D267-D270, DOI: 10.1093/nar/gkh061.
Brandt, M., et al., "Mapping Orphanet Terminology to UMLS", AIME 2011, LNAI 4747, pp. 194-203, 2011.
Harrow, I., et al., "Matching disease and phenotype ontologies in the ontology alignment evaluation initiative", Journal of Biomedical Semantics (2017), 8:55, DOI 10.1186/s13326-017-0162-9.
General equivalence maps 2018 icd-10-pcs., 2018 Official ICD-10-PCS Coding Guidelines 2018 Version Update Summary. 2 pages.
Faria, D., "Tackling the challenges of matching biomedical ontologies", Journal of Biomedical Semantics (2018) 9:4, DOI 10.1186/s13326-017-0170-9, 19 pages.
Bodenreider, O., "Using SNOMED CT in combination with MedDRA for reporting signal detection and adverse drug reactions reporting", AMIA 2019 Symposium Proceedings, 5 pages.
Dhombres, F., et al., Interoperability between phenotypes in research and healthcare terminologies—Investigating partial mappings between HPO and SNOMED CT, Journal of Biomedical Semantics (2016), 7:3, DOI 10.1186/s13326-016-0047-3, 13 pages.
Stoilos, G., et al., "A novel approach and Practical Algorithms for Ontology Integration".
Arora, S., et al., "A simple but tough-to-beat Baseline for Sentence Embeddings", published as a conference paper at ICLR 2017, 16 pages.
Thieblin, E., et al., "Task-Oriented Complex Ontology Alignment: Two Alignment Evaluation Sets", Nature 2018, 655-670, ESWC 2018, LNCS 10843, https://doi.org/10.1007/978-3-319-93417-4_42.
Razzaki, S., et al., "A comparative study of artificial intelligence and human doctors for the purpose of triage and diagnosis", Babylon Health, Jun. 27, 2018, 15 pages.
Barisevicius, G., et al,. "Supporting Digital Healtcare Services Using Semantic Web Technologies", ISWC 2018, LNCS 11137, pp. 291-306, 2018, https://doi.org/10.1007/978-3-030-00668-6_18.
Horrocks, I., et al., "From SHIQ and RDF to OWL: The Making of a Web Ontology Language", 31 pages. http://www.cs.man.ac.uk/~horrocks/Publications/download/2003/HoPH03a.pdf.
Stoilos, G., "Methods and Metrics for Knowledge Base Engineering and Integration", 15 pages, http://ceur-ws.org/Vol-2195/research_paper_4.pdf.
Salvadores, M., "BioPortal as a Dataset of Linked Biomedical Ontologies and Terminologies in RDF", IOS Press and authors, 2009, 8 pages.
Callahan, A., et al., "Bio2RDF Release 2: Improved coverage, interoperability and provenance of Life Science Linked Data", ADFA, p. 1, 2011, 14 pages.
McCray, A. T., "The Representation of Meaning in the UMLS, Methods of Information in Medicine", 34: 193-201, 1995.
Ritze, D., "Linguistic Analysis for Complex Ontology Matching", 12 pages, http://publications.wim.uni-mannheim.de/informatik/lski/ritze2010complexmatchlinguistic.pdf.
Zhelezniak, S., "Don't Settle for Average, Go for the Max: Fuzzy Sets and Max-Pooled Word Vectors", published as a conference paper at ICLR 2019, 17 pages.
Cer, D., et al., "Universal Sentence Encoder", Apr. 12, 2018, 7 pages.
Euzenat, J., "Semantic Precision and Recall for Ontology Alignment Evaluation", IJCAI 2007, pp. 348-353.

* cited by examiner

SYSTEM AND METHOD FOR ENABLING INTEROPERABILITY BETWEEN A FIRST KNOWLEDGE BASE AND A SECOND KNOWLEDGE BASE

FIELD

Embodiments described herein relate to methods and systems for enabling interoperability between a first knowledge base and a second knowledge base, when the first and second knowledge bases are encoded according to different coding standards.

BACKGROUND

A diagnostic system may include a knowledge base that may be represented graphically. The knowledge base may include a plurality of entities in the form of nodes. The entities may define concepts, which may be medical concepts. The knowledge base may also include a plurality of relations between the entities. Different knowledge bases may be linked in order to expand the knowledge base since a user may only be registered with one knowledge base, for example.

BRIEF DESCRIPTION OF THE FIGURES

The subject-matter of the present disclosure is best described with reference to the accompanying figures, of which.

DETAILED DESCRIPTION OF THE EMBODIMENTS

It is an object of the present disclosure to improve on the prior art. In particular, the present disclosure addresses one or more technical problems tied to computer technology and arising in the realm of computer networks, in particular the technical problems of memory usage and processing speed. The disclosed methods solve this technical problem using a technical solution, namely by identifying an entity in a second knowledge base that matches an entity in a first knowledge base and creating a link between the matched entities. In this way a link is a one-to-one mapping. One-to-one mappings between knowledge bases reduce the amount of processing power required when subsequently linking the knowledge bases during use. For example, when connecting a second knowledge base to a first knowledge base, fewer iteration cycles will be required compared to a case where many-to-one mappings, or one-to-many mappings are employed. In addition, a higher degree of confidence can be achieved in the resulting connection. In addition, other embodiments specifically relate to reducing multiplicity mappings, e.g., one-to-many or many-to-one mappings, to one-to-one mappings. In addition, other embodiments provide methods and systems for connecting a third knowledge base to a first knowledge base via a central, second knowledge base. In this way, sets of one-to-one mappings will only be required to and from the entities/nodes of the second knowledge base. Accordingly, fewer mappings are required to be stored compared to a case where every knowledge base could be connected to every other knowledge base directly, which would require an increased number of mappings.

Figure 1:
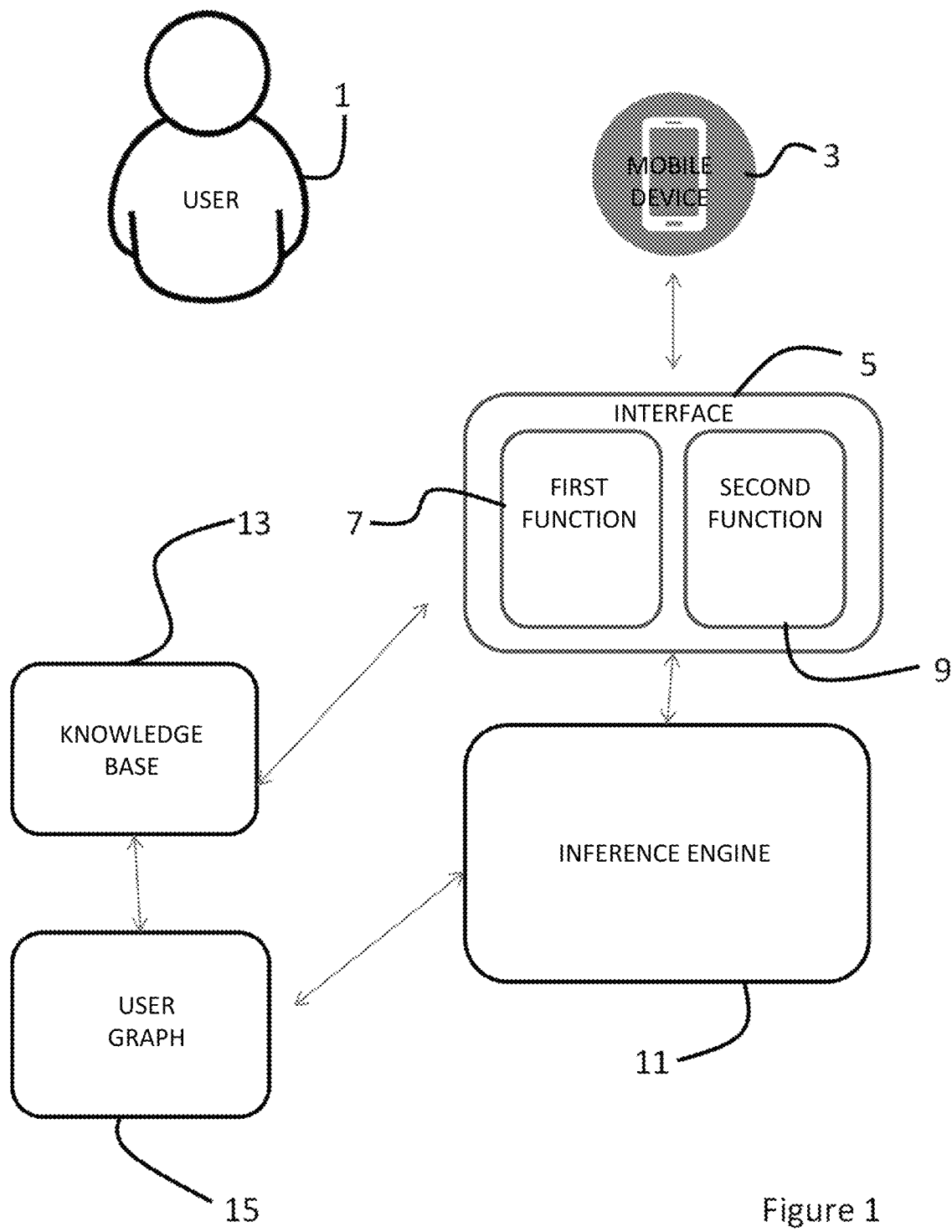
FIG. 1 shows a block diagram of the diagnostic system.

With reference to FIG. 1, a user 1 communicates to a diagnostic system via a mobile phone 3. However, any device could be used, which is capable of communicating information over a computer network, for example, a laptop, tablet computer, information point, fixed computer, voice assistant, etc.

The mobile phone 3 will communicate with interface 5. Interface 5 has two primary functions; the first function 7 is to take the words uttered by the user and turn them into a form that can be understood by the inference engine 11. The second function 9 is to take the output of the inference engine 11 and to send this back to the user's mobile phone 3.

In some embodiments, Natural Language Processing (NLP) is used in the interface 5. NLP is one of the tools used to interpret, understand, and then use every day human language and language patterns. It breaks both speech and text down into shorter components and interprets these more manageable blocks to understand what each individual component means and how it contributes to the overall meaning, linking the occurrence of medical terms to the knowledge base. Through NLP it is possible to transcribe consultations, summarise clinical records, and chat with users in a more natural, human way.

However, simply understanding how users express their symptoms and risk factors is not enough to identify and provide reasons about the underlying set of diseases. For this, the inference engine 11 is used. The inference engine 11 is a powerful set of machine learning systems, capable of reasoning on a space of more than hundreds of billions of combinations of symptoms, diseases and risk factors, per second, to suggest possible underlying conditions. The inference engine 11 can provide reasoning efficiently, at scale, to bring healthcare to millions.

In an embodiment, a knowledge base 13 is a large structured set of data defining a medical knowledge base. The knowledge base 13 describes an ontology, which in this case relates to the medical field. It captures human knowledge on modern medicine encoded for machines. This is used to allow the above components to speak to each other. The knowledge base 13 keeps track of the meaning behind medical terminology across different medical systems and different languages. In particular, the knowledge base 13 includes data patterns describing a plurality of semantic triples, each including a medical related subject, a medical related object, and a relation linking the subject and the object. An example use of the knowledge base would be in automatic diagnostics, where the user 1, via mobile device 3, inputs symptoms they are currently experiencing, and the inference engine 11 can deduce possible causes of the symptoms using the semantic triples from the knowledge base 13.

A user graph 15 is also provided and linked to the knowledge base 13.

Figure 2:
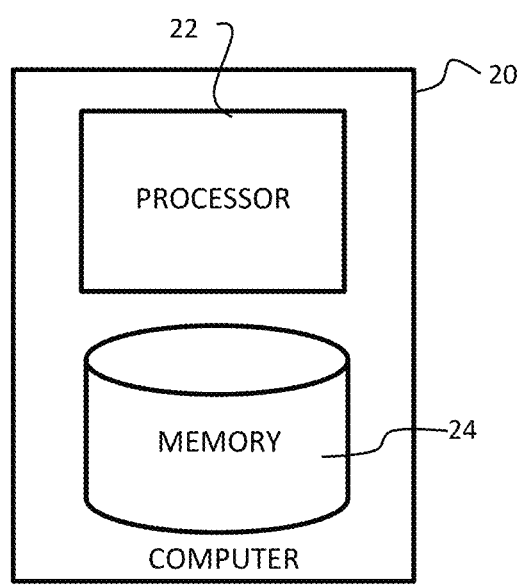
FIG. 2 shows a computer for implementing the diagnostic system from FIG. 1.

With reference to FIG. 2, a computer 20 is provided to enable the inference engine 11 and the knowledge base 13 (from FIG. 1) to operate. The computer 20 includes a processor 22 and a memory 24. The memory 24 may include a non-transitory computer-readable medium for storing electronic data. The memory 24 may refer to permanent storage. The electronic data may include instructions which, when executed by the processor 22, cause the processor to perform one or more of the methods described herein.

Figure 3:
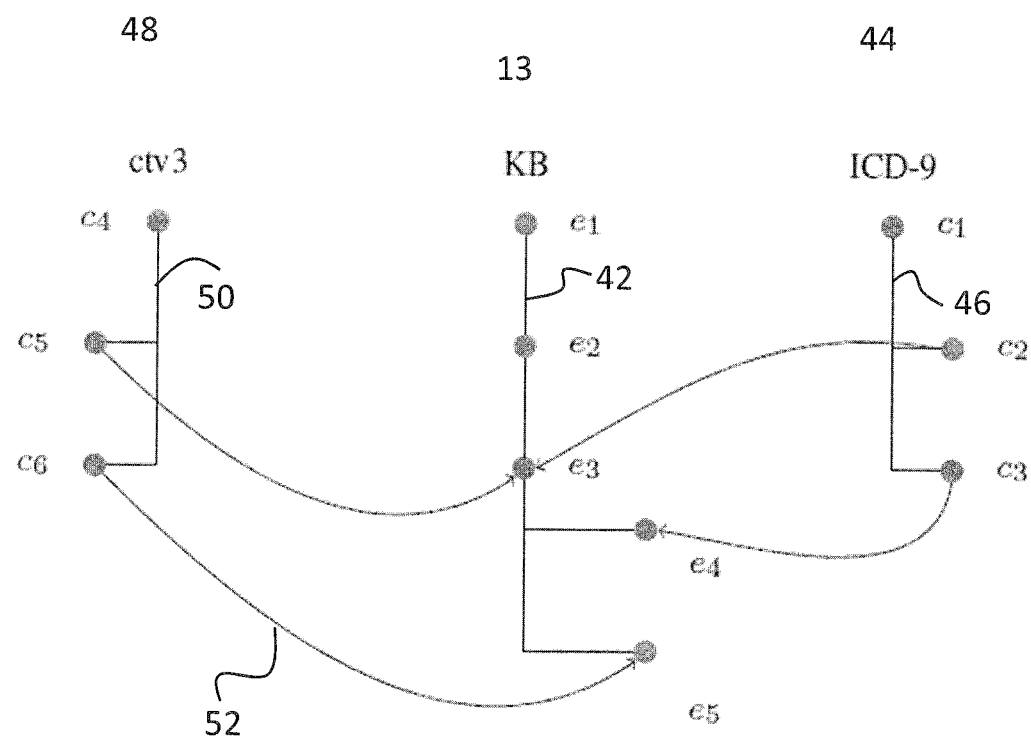
FIG. 3 shows three knowledge bases, a central one of which forms part of the diagnostic system from FIG. 1.

With reference to FIG. 3, a first knowledge base 44 includes a plurality of entities (c1-c3). The entities (c1-c3) are linked by a plurality of relations 46. Similarly, a second knowledge base 13 includes a plurality of entities (e1-e5). The plurality of entities (e1-e5) of the second knowledge base 13 are linked by relations 42. In addition, a third knowledge base 48 includes a plurality of entities (c4-c6). The plurality of entities from the third knowledge base 48 are linked by a plurality of relations 50. As used herein, the second knowledge base 13 may be referred to as the (central) knowledge base (KB), and the first and third knowledge bases 44, 48 may be referred to as coding systems. However, in some embodiments, the terms "first," "second," and "third," may be used interchangeably when referring to the knowledge bases.

The first, second, and third knowledge bases 44, 13, and 48, may define medical ontologies. The second, central, knowledge base 13 may be encoded using Systematized Nomenclature of Medicine Clinical Terms (SNOMED CT). The first knowledge base 44 may be encoded using International Classification of Diseases (ICD) coding standard. There are various revisions of ICD, for example ICD-9 and ICD-10 being the ninth and tenth revisions of the ICD coding standard. The third knowledge base 48 may be encoded using Real Codes of clinical terms (CT). There are various revisions of CT, for instance ctv3 is the third revision. In this way, the first, second, and third knowledge bases are each encoded according to different coding standards.

It has been recognised that interoperability between electronic health records, stored for example as knowledge bases 13, 44, and 48, is a key problem and objective in modern healthcare. More precisely, it would be beneficial if health organisations using different coding systems where able to exchange data with each other for epidemiological, statistical, or research purposes. To provide means to translate data from one coding standard to the other, mappings between them can be used.

In FIG. 3, mappings are shown as links 52. The links 52 extend between entities from different knowledge bases 13, 44, and 48. In particular, the links 52 extend between entities from a first knowledge base 44 and a second knowledge base 13, and between entities from the second knowledge base 13 and the third knowledge base 48. More specifically, links extend from entities from the third knowledge base 48 to entities from the second knowledge base 13. In addition, links extend from entities from the first knowledge base 44 to entities from the second knowledge base 13.

Formally, a KB is a set of triples of the form <s p o>, (subject, property, and object). Entities that appear in the subject position are also called classes (e.g., Malaria, Fever, etc.), whereas in the object position it is possible to have either classes or literals (strings, numbers, or boolean values).

Using a resource description framework (RDF), it is possible to capture class properties (e.g., <Malaria causedBy Plasmodium>), class labels (e.g., <MyocardialInfarction label "Heart Attack">), and class subsumptions (e.g., <VivaxMalaria subClassOf Malaria>). For a class e the notation e.ℓ is used to refer to its label. Statements can be given formal semantics (meaning) and especially subsumption triples state that the subject needs to be understood (interpreted) as a more specific entity than that of the object. Sets of subsumptions are used to organise classes in KBs into so-called hierarchies or taxonomies. For some KB K and triple tr we write K ⊨ tr where ⊨ denotes resource development framework schema (RDFS) entailment. For example, consider the following KB:

K={<VivaxMalaria subClassOf Malaria>, <Malaria subClassOf Coccidiosis>}

Then, K ⊨ <VivaxMalaria subClassOf Coccidiosis>. KBs can be identified and distinguished between each other using International Resource Identifiers (IRIs) or for simplicity short names. For kb the name of a KB and e, one of its entities, can be written as kb:e if it is desirable to emphasise that this entity appears in that particular KB. An entity with the same name but different IRI may appear in a different KB kb' and hence we can write kb':e.

The central, second KB 13 described herein is developed by integrating various well-known medical KBs, like SNOMED CT, NCI, and more, using a novel matching and integration approach. Given a "current" instance of the KB $K_i$ and a new data source K, a new version $K_{i+1}$ is created by enriching $K_i$ with information from K. To perform the enrichment process the common entities between $K_i$ and K are identified using matching algorithms while for every unmatched entity in K a new entity in $K_i$ is created. Key parts of this procedure are described in the following example.

Example 1. Assume that SNOMED CT (sct) is the first current KB $K_i$. Although SNOMED CT is a large and well engineered KB, relevant and useful medical information is still missing. For example, for the disease "Ewing Sarcoma" it only contains the triple <sct:EwingSarcoma subClassOf sct:Sarcoma> and no relations to signs or symptoms. In contrast, the NCI KB $K_{nci}$ contains the following triple about this disease:

<nci:EwingSarcoma mayHaveSymptom nci:Fever>

Matching can be used to establish links between the related entities in $K_i$ and $K_{nci}$ and then use the latter in order to enrich $K_i$. More precisely, using a matching algorithm it is possible to identify the following mappings:

sct:EwingSarcoma↔nci:EwingSarcoma sct:Fever↔nci:Fever

These mappings can be used to "copy" information from K to $K_i$, for example, given the above mappings, the triple <sct:EwingSarcoma mayHaveSymptom sct:Fever> can be introduced.

Then, the enriched KB would contain the knowledge that "Ewing sarcoma may have fever as a symptom."

If for an entity e in $K_{nci}$ no mapping to any entity in $K_i$ exists, then a new entity e' is introduced and then the triples associated to e in $K_{nci}$ are transferred to e'. The above approach can be used to enrich $K_i$ with any type of information, like lexical or even a hierarchical one.

The quality and integrity (semantic, structural, and label) of the enriched KB is monitored using various automatically extracted metrics. In addition, its medical validity is also monitored using manual doctor verification.

This approach creates a highly unified medical KB which differentiates it from existing approaches to biomedical corpora like the Unified Medical Language System (UMLS), BioPortal, and Bio2RDF which follow a Linked Open Data (LOD) approach. In these approaches, different sources reside under their original codes and their level of unification is usually low, making it hard to build services on top of them.

The first KB 13 may contain 1,5 m concepts, 220 properties, and 12 m subsumptions and it may be loaded in an in-memory RDF4J triple-store instance. Following the UMLS model, 93 classes in the KB have been annotated as semantic types (stys) which denote abstract categories, e.g., <Disease is_sty true> while every other class is assigned to at least one semantic type, e.g., <Malaria has_sty Disease>.

To be able to provide an interoperability framework for existing coding and classification systems (first and third knowledge bases 44, 48, in FIG. 3), it is possible to integrate them in the second KB 13 and use it as a mediator over which translations and mappings between them are occurring. This can be done using an integration framework discussed above. Unfortunately, in many cases, such sources are constructed as classification and multi-faceted systems and the subsumption relations they include do not follow the strict model-theoretic semantics of languages like RDF.

Consequently, in order not to "pollute" the first KB 13 hierarchy with subClassOf relations that do not reflect actual taxonomic information, a new integration pipeline was designed. Alignment and matching algorithms may be used to discover mappings between the coding system and the Babylon Health KB, however, in the integration (merging) phase no hierarchical axioms are "copied" to the current version of the first KB 13. Instead, a new relation hasCode between the mapped entities is introduced and the taxonomic arrangement of codes in the coding system 44, 48 are kept in a separate part of the first KB 13. FIG. 3 depicts graphically the model by which coding systems 44, 48 are integrated in the system. Intuitively, the second KB 13 hierarchy sits in the center while entities (c1-c6) from the different coding system 44, 48 are linked to entities (e1-e5) in the second KB 13 with the hasCode relation 52.

Due to differences in granularity between terminologies, not all codes in a coding system 44, 48 are expected to be mapped to some entity (e1-e5) in the second KB 13. Services developed in the diagnostic system (like prescriptions, etc.) operate on the second KB 13 and it would be unfeasible to adapt the services to the coding systems 44, 48 used in different countries whenever the services are deployed in them. Yet, local doctors and users would be accustomed to prescribe and diagnose using names and codes of the coding system 44, 48 that is used locally. Due to this requirement, the second KB 13 may contain an image entity for every code of a coding system 44, 48 that is integrated into it. If for some code c the matching algorithm was not able to find a corresponding (equivalent) second KB 13 entity during alignment, then a new entity e' should be created and a triple <e' hasCode c> is added.

Figure 4:
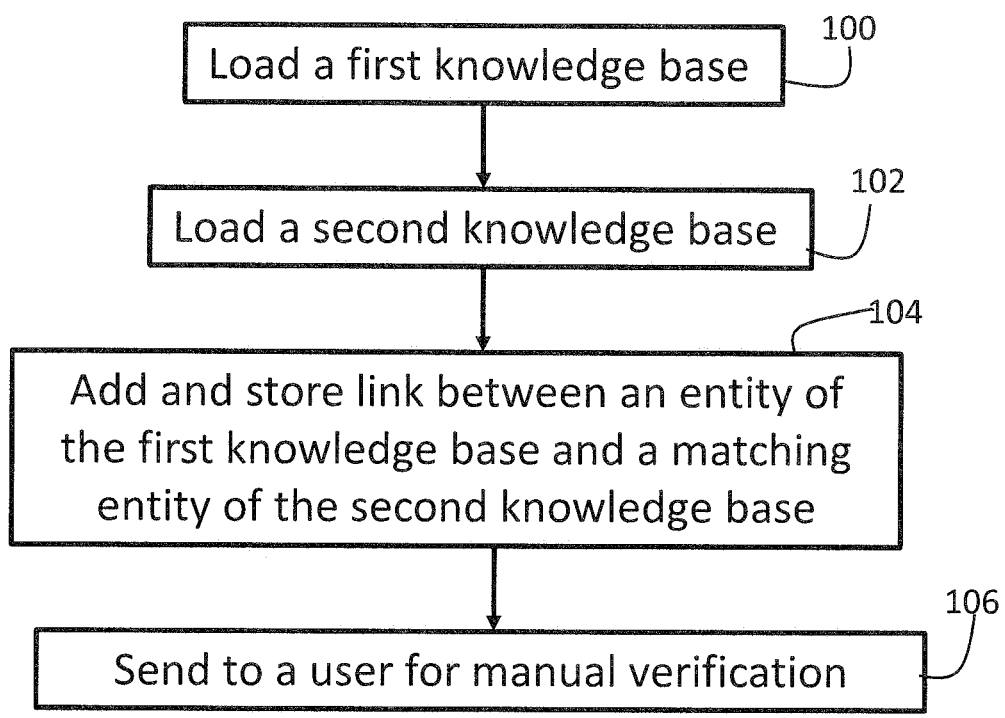
FIG. 4 shows an embodiment of a method of enabling interoperability between the central knowledge base and the first or third knowledge base from FIG. 3.

With reference to FIG. 4, overall, the present integration method includes the steps of loading 100, 102 the first knowledge base 44 (coding system) and the second knowledge base 13. The method also includes adding and storing a link 52 between an entity c2 from the first knowledge base 44 and a matching entity e3 from the second knowledge base 13. The link is a one-to-one mapping. Importantly, one-to-one mappings reduce the amount of processing power required when ultimately connecting knowledge bases since fewer iterations are required compared to a case where multiplicity mappings are employed. Finally, the link may be sent to a user to verify the match between the entities e3 and c2.

Due to granularity differences, matching algorithms often compute mappings of high multiplicity, that is, they map one entity from one source to many entities in the other. To avoid ambiguity issues, all mappings of high multiplicity may be reduced to one-to-one mappings. In summary, design and application requirements imposed the following properties on the relation hasCode:

1. It needs to be a functional and inverse functional, that is, only one entity (e1-e5) from the second KB 13 to be associated to any given coding system 44, 48 entity (c1-c6) and vice versa.
2. It needs to contain a representative (e1-e5) from the second KB 13 for every coding system 44, 48 entity (c1-c6).

To satisfy property 1, mappings of higher multiplicity need to be reduced to one-to-one mappings. Our approach to do this is the following:

$D_{1-m}$: for the case where m codes $c_i$ are mapped to one second KB entity e, we create m different entities in the second KB 13 $e_i$, add triples <$e_i$ hasCode $c_i$> and then also subsumption triples <$e_i$ subClassOf e>.

Figure 5:
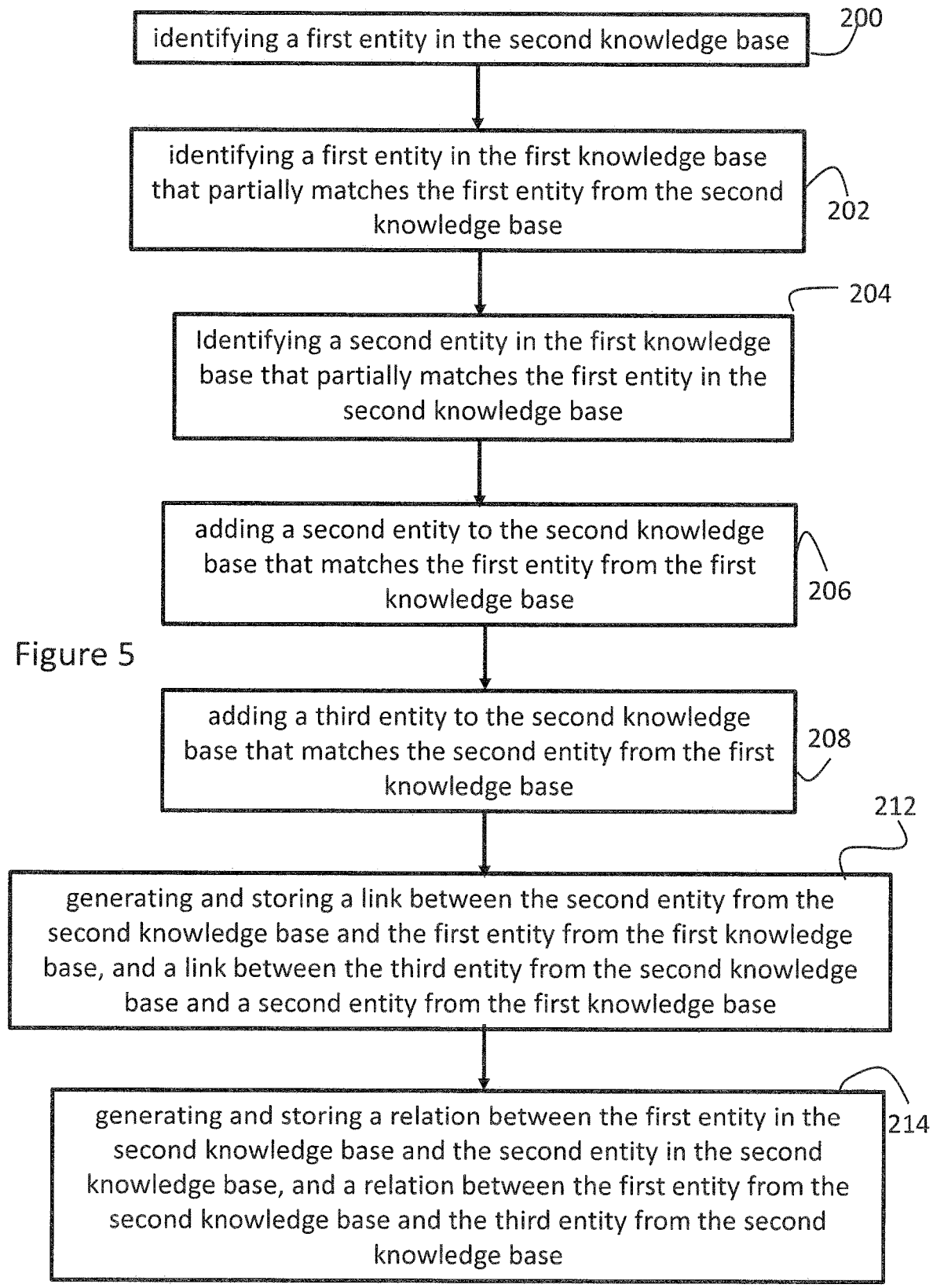
FIG. 5 shows an embodiment of a method of adding and storing a link between matching entities of the knowledge bases from FIG. 3.

In other words, with reference to FIG. 5, an embodiment for generating one-to-one mappings between entities from different knowledge bases is provided for a situation where two or more entities in the first knowledge base at least partially map to one entity in the second knowledge base 13, in a form of many-to-one mappings between the first and second knowledge bases.

At step 200, a first entity (e2) is identified in the second knowledge base 13. Next, at step 202, a first entity (c2) is identified in the first knowledge base 44 that partially matches the first entity (e2) in the second knowledge base 13. Next, at step 204, a second entity (c3) is identified in the first knowledge base 44 that partially matches the first entity. The second entity (c3) from the first knowledge base 44 and the first entity (c2) from the first knowledge base 44 may be taxonomically related. In other words, the second entity (c3) may be a sub-class of the first entity (c2), or vice versa.

Identifying the first and second entities (c2, c3) from the first knowledge base 44 may include searching the first knowledge base 44 for one or more labels at least partially matching a label of the first entity (e2) from the second knowledge base 13. The searching may include a key word search. Matching may be considered as an exact linguistic match of the labels of the entities being compared. Partial matching may be that one entity includes a key word included in the other compared entity. For instance, one entity may be Malaria, and the other entity may be Vivax Malaria. This may be considered a partial entity.

The method may also include, at step 206, adding a second entity (e3) to the second knowledge base 13 that matches the first entity (c2) from the first knowledge base 44. At step 208, the method also includes adding a third entity (e4) to the second knowledge base 13.

The second entity (e3) added to the first knowledge base 13 may match the first entity (c2) from the first knowledge base 44. The third entity (e4) added to the first knowledge base 13 may match the second entity (c3) from the first knowledge base 44.

Next, at step 212, a link may be generated between the first entity (c2) from the first knowledge base 44 and the second entity (e3) from the second knowledge base 13. In addition, a link may be generated between the third entity (e4) from the second knowledge base 13 and the second entity (c3) from the first knowledge base 44. The links 52 may be stored in the memory 22 (FIG. 2).

A relation (subclass) may be generated at step 214 between the first entity (e2) in the second knowledge base 13 and the second entity (e3) of the second knowledge base 13. Also at step 214, a relation (subClass) may be generated between the first entity (e2) from the second knowledge base 13 and the third entity (e4) from the second knowledge base 13. The relation may be stored in the memory 22 (FIG. 2).

Storing one-to-one mappings in this way provides several benefits. For instance, less processing is ultimately required when connecting knowledge bases subsequently during use compared to a case where one-to-many mappings have been created.

$D_{m-1}$: for the case where m second KB entities $e_i$ are mapped to a single coding system code c, we proceed as follows: we pick one of the entities $e_k$ with the highest scored mapping $e_k \leftrightarrow c$ and add $<e_k$ hasCode c> and, finally, add triples of the form $<e_i$ related $e_k>$ for all other $1 \leq i \leq m$ for $i \neq k$ entities.

Figure 6:
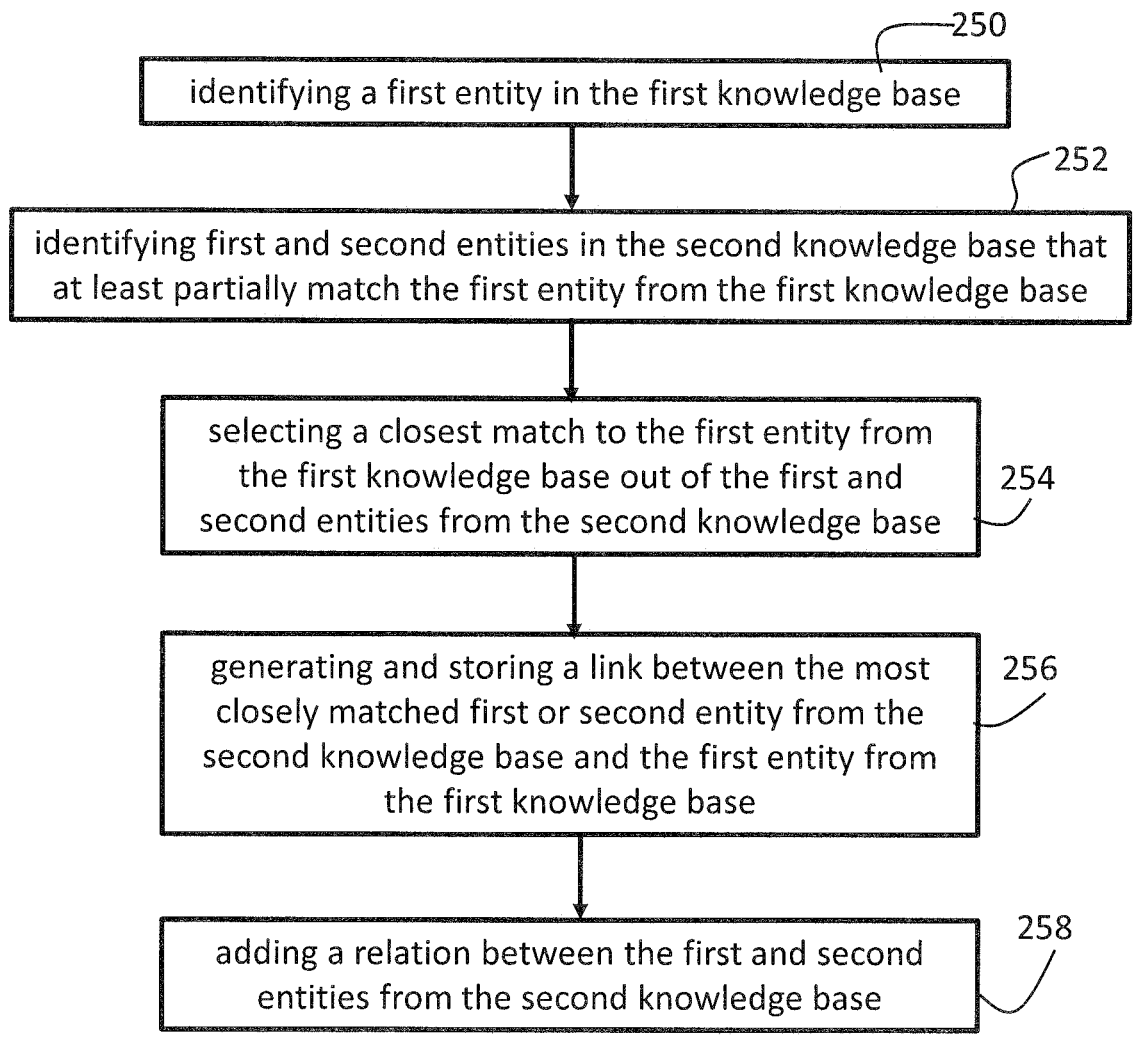
FIG. 6 shows an embodiment of a method of adding and storing a link between matching entities of the knowledge bases from FIG. 3.

In other words, with reference to FIG. 6, a further embodiment is provided for a case where more than one entity from the second knowledge base 13 is at least partially mapped to a single entity of the first knowledge base 44.

At step 250, a first entity (c1) is identified in the first knowledge base 44. At step 252, first and second entities (e1, e2) are identified in the second knowledge base 13 that at least partially match the first entity (c1) from the first knowledge base 44. At step 254, a closest match is selected out of the first and second entities (e1, e2) from the second knowledge base 13 and the first entity (c1) from the first knowledge base 44. At step 256, a link is generated between the most closely matched first or second entities (e1, e2) from the second knowledge base 13 and the first entity (c1) from the first knowledge base 44. In addition, a link may be stored as electronic data in the memory 22 (FIG. 2). Furthermore, a relation between the first and second entities (e1, e2) from the second knowledge base 13 may be added.

Selecting a closest match at step 254 may comprise determining a distance between labels of the first and second entities (e1, e2) and entity (c1). The distance may be determined using a vector approach. For instance, the distance between labels of the first and second entities (e1, e2) of the second knowledge base 13 and entity c1 of the first knowledge base 44 may be determined by obtaining a vector of each of the first and second entities (e1, e2) from the second knowledge base 13 and a vector of the first entity (c1) from the first knowledge base 44. Next, the entities (e1, e2) from the second knowledge base 13 may be ranked according to distance. In turn, the closest match may be determined as the entity with the closest distance to the first entity (c1) of the first knowledge base 44.

The entities in the first and second knowledge bases may include a label. Identifying the first and second entities (e1, e2) from the second knowledge base 13 at step 252 may involve searching the second knowledge base 13 for a label at least partially matching a label of the first entity from the first knowledge base. At least partially matching has the same definition as used above in the embodiment from FIG. 5. The searching may include a key word search. This method of scoring and ranking entities is discussed in more detail above.

In this way, a multiplicity mapping is reduced to one-to-one mappings. Specifically, many-to-one mappings are reduced to one-to-one mappings. Beneficially, one-to-one mappings reduce the amount of processing required when connecting different knowledge bases during use, since fewer iterations will be required to connect between entities/nodes, of the different knowledge bases.

Overall the present mapping approach is depicted in Algorithm 1 below.

| Algorithm 1 |
|---|
| Algorithm 1 CodingIntegration($\mathcal{K}$, $\mathcal{C}$, $\mathcal{M}$) |
| Input: The current KB $\mathcal{K}$, a coding system $\mathcal{C}$, and a set of "expert" mappings.<br>//Map KBs using expert alignments and additional alignment methods, first take 1-1 mappings.<br>1: $M_c$ := oneToOne($\mathcal{M}$)<br>2: $M_+$ := try to map all unmapped elements in $\mathcal{C}$ using label matching with high threshold, e.g., 0.9<br>3: $M_c$ := $M_c \cup \{m' \in \mathcal{M}_+ \vert$ no m $\in M_c$ exists with Sig(m') $\cap$ Sig(m) = $\emptyset\}$<br>//For non 1-1 mappings reduce them to 1-1 by using approaches the approaches $D_{1-m}$ and $D_{m-1}$.<br>4: $M_r$ := $(M \cup M_+) \setminus M_c$.<br>5: Build clusters of m-1 and 1-m mappings for mappings in $M_r$.<br>6: For every m-1 (resp. 1-m) cluster follow approach in $D_{m-1}$ (resp. $D_{1-m}$).<br>//For unmapped codes create new entities in KB and apply heuristics to link them.<br>7. For all codes c $\in \mathcal{C}$ that have no mapping in $\mathcal{M}$, create a new entity e in $\mathcal{K}$ B and add (e hasCode c).<br>8: Use heuristics to find e' $\in \mathcal{K}$ and add triple (e subClassOf e'). |

Figure 7:
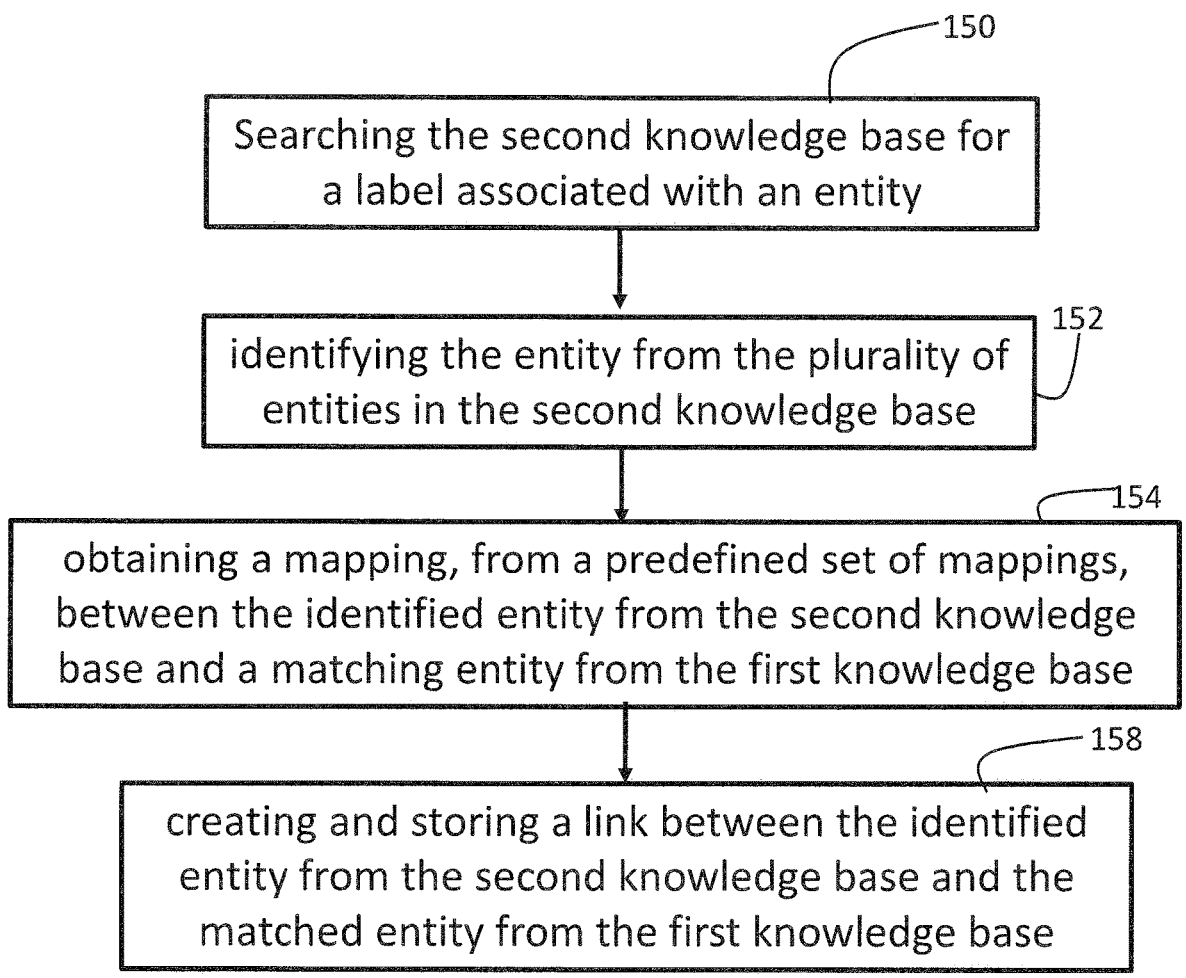
FIG. 7 shows a further embodiment of a method of adding and storing a link between matching entities of the knowledge bases from FIG. 3.

The detail of Algorithm 1 is described below. However, in summary, with reference to FIG. 7, there is provided an embodiment where a pre-defined set of one-to-one mappings are used to map entities from the coding systems and the second knowledge base 13, as described above.

The method includes searching a second knowledge base 13 for a label associated with an entity, at step 150. At step 152, the entity from the second knowledge base 13 having the label is identified. At step 154, a mapping is obtained. The mapping is a one-to-one mapping. The mapping may be selected from a predefined set of mappings. The mappings may be between the identified entity from the second knowledge base 13 and a matching entity from the first knowledge base 44.

At step 158, a link is created between the identified entity from the second knowledge base 13 and the matched entity from the first knowledge base 44. The link effectively reflects the one-to-one mapping from the pre-defined list, and the link is stored so as to be retrievable subsequently, for example, when connecting a third knowledge base 48 to the first knowledge base 44, via the second knowledge base 13 which acts as a central hub. The link is stored in the memory 22 (FIG. 2). By storing one-to-one mappings as links in this way ultimately reduces processing power when connecting the third to first knowledge bases since fewer iterations will be required. Generating the links from pre-defined one-to-one mappings saves processing power by obviating the need to derive the one-to-one mappings using other means, for example by label matching of entities in the first and second knowledge bases 44, 13.

In this way, one-to-one mappings between matched entities in the first and second knowledge bases 44, 13 are generated. Storing mappings having a single, or one-to-one, relationship between entities reduces the required memory usage since each mapping is associated with only two entities.

In more detail, Algorithm 1 loads the second KB 13 (K), the coding system C 44 and a set of "expert" mappings (M), that is, mappings published by third parties (NHS, SNOMED CT, etc.). The algorithm is divided into three phases. First, and due to property 1 above, the one-to-one mappings from the expert mappings are extracted. Subsequently, label matching methods based on class label similarity may be used in an attempt to compute more mappings ($M_+$) which are then integrated into $M_c$. Only the newly created mappings that involve entities not already mapped in $M_c$ to some entity are copied; this is achieved by checking the signature of the computed mappings using function Sig which returns the set of entities involved in a mapping. At the second phase, the algorithm processes mappings of higher multiplicity using the two approaches outlined in $D_{1-m}$, and $D_{m-1}$.

Finally, in an effort to satisfy property 2 described above, unmapped codes are used to introduce new entities in the first KB 13 and appropriate hasCode relations are added between them. The new entities are linked to the existing KB 13 hierarchy using various heuristics. The heuristic may be the following:

If for some unmapped entity c ∈ C one of its parent in C is mapped to some entity $e_{kb}$ ∈ K (i.e., we have <c subClassOf c'> ∈ C and <$e_{kb}$ hasCode c'>), then a new entity e' is created in K and <e' subClassOf $e_{kb}$> and <e' hasCode c'> may be added to K.

Figure 8:
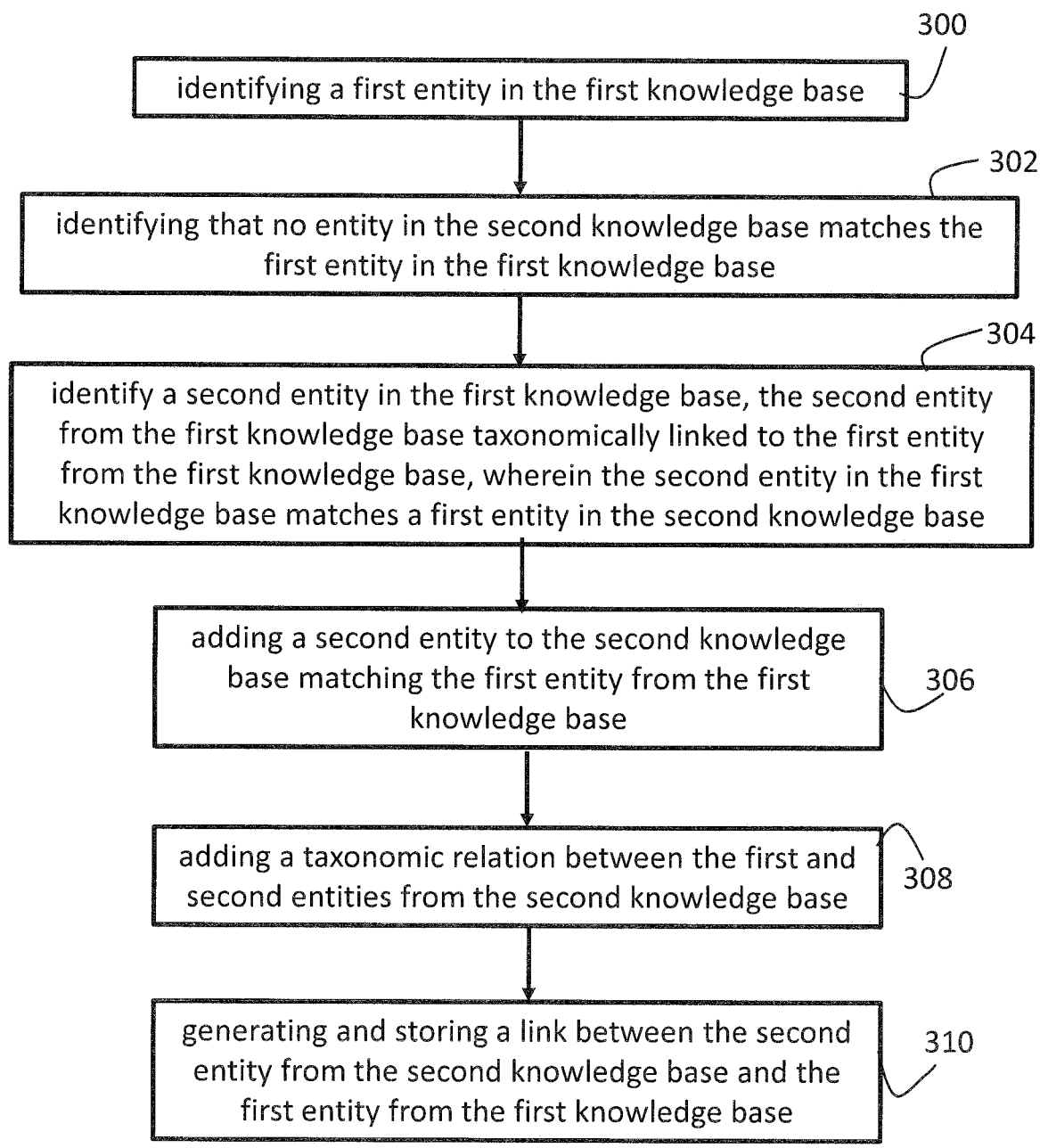
FIG. 8 shows a further embodiment of a method of adding and storing a link between matching entities of the knowledge bases from FIG. 3.

In other words, with reference to FIG. 8, a further embodiment is provided for a case where no entity in the second knowledge base 13 exists for an entity identified from the first knowledge base 44.

At step 300, a first entity (c1) in the first knowledge base 44 is identified. Next, at step 302, it is found that, when searching the second knowledge base 13, no matching entity is found for the first entity (c1) from the first knowledge base 44. Next, at step 304, a second entity (c2) is identified in the first knowledge base 44, the second entity (c2) being taxonomically linked to the first entity (c1) from the first knowledge base 44. The second entity (c2) in the first knowledge base 44 may match a first entity (e1) in the second knowledge base 13.

Identifying that no entity from the second knowledge base 13 matches the first entity (c1) from the first knowledge base 44 may include performing a search for a label that matches the first entity (c1) from the first knowledge base 44, and returning no matches. The search may be a key word search. In such a case, the words included in the labels of the entity (c1) from the first knowledge base 44 may not be present in any of the labels from entities (e1-e5) from the second knowledge base 13.

Next, at step 306, a second entity (e2) is added to the second knowledge base 13 that matches the first entity (c1) from the first knowledge base 44. Next, at step 308, a relation is added between the first and second entities (e1, e2) from the second knowledge base 13 (using the function subClass). Next, at step 310, a link is generated between the second entity (e2) of the second knowledge base 13 and the first entity (c1) from the first knowledge base 44. The link 52 is stored as electronic data in the memory 22 (FIG. 2).

Again, it is possible to map the entities from the first coding system 44 to the second knowledge base 13 in a one-to-one manner, even when no entity exists in the second knowledge base 13 that matches the entity identified in the first knowledge base 44. As a result of the one-to-one mapping relationship, enabling one-to-one access between entities of the first and second knowledge bases 44, 13, when linking the knowledge bases subsequently during use.

The above heuristic can be applied in a recursive way. That is, if for some entity the above condition does not hold (i.e., none of its parents is mapped to some entity in the KB), then the condition is first applied to some of its parents in order to create some image entity for the parents. This process is complemented and validated by in-house doctors and KB engineers to assert the correctness of the hierarchy and the medical information.

Due to property 1 of relation hasCode, from any given code $c_1$ ∈ $C_1$ we can trivially navigate to some entity $e_{kb}$ via the single triple <$e_{kb}$ hasCode $c_1$>. Hence, the problem of navigating from $c_1$ ∈ $C_1$ to some code in $C_2$ boils down to navigating from $e_{kb}$ to $C_2$. If some triple <$e_{kb}$ hasCode $c_2$> with $c_2$ ∈ $C_2$ also exists, then $c_2$ is trivially a best matching code to $c_1$. Things become more involved if such a triple does not exist. In that case some close match to $e_{kb}$ needs to be returned using a form of so-called partial mappings.

The problem of returning some close match for an unmatched entity is referred to as complex or partial ontology matching. Approaches for computing partial mappings between two terminologies have been investigated in the area of biomedical ontologies. Dhombres studied the use of both lexical (so-called demodification) and logical techniques to compute such partial mappings and their evaluation showed that the logical approach usually behaves better, hence we also adopt it here. Intuitively, if some entity e is not mapped, then the approach looks for some ancestor of e that is mapped hence performing some type of hierarchy traversal. Formally, we assume the function getCodes which is defined as follows:

Definition 2. For some entity $e_{kb}$ in the KB and a target coding system C, getCodes ($e_{kb}$, C) returns either a singleton set {c} if c ∈ C exists such that <$e_{kb}$ hasCode c> ∈ K, or a set containing exactly all codes c ∈ C such that the following hold:

1. K ⊨ <$e_{kb}$ subClassOf e>;
2. {{<e hasCode c>},{<e related $e_r$>, <$e_r$ hasCode c>}} ∩ K≠∅; and
3. no e' ∈ K such that K ⊨ <e' subClassOf e> and that satisfies the above properties exists.

Different types of heuristics to score, order, or assess whether the returned codes are vague or not may be investigated and would be beneficial for such a translation service.

In order to provide with means to assess the precision of the returned codes, the problem is modelled as an information retrieval one. Intuitively, when a doctor wants to map some unmapped entity e to a coding system C they look at the label of entity e and search on the index of C for entities with similar labels. Method for retrieving document for textual queries include ElasticSearch, sentence embeddings or even string similarity approaches. Sentence embeddings is a modern method that attempts to capture the contextual similarity between words and sentences. Every sentence (or word) is mapped to a vector in some vector space with the property that (semantically) similar sentences are clustered closely in the space. Vectors for words are learned through an unsupervised learning phase and by training over large corpora of text. For example, the vectors learned for words "Paracetamol" and "painkiller" are expected to be clustered closely in the vector space since they tend to occur often in text and speak about "similar" things. Given vectors for words and vectors for sentences can be computed using various different models.

The overall navigation and scoring approach is depicted in Algorithm 2. Given some KB entity e to be translated into some target coding system C, the algorithm first uses method getCodes to get a set (or singleton) of codes for e on C.

If a singleton set {c} is returned, then according to Definition 2 this means that a direct link from e to c exists and c is returned with confidence 1. If a set of codes is returned, then this means that ancestors and the hierarchy of the KB are exploited. Subsequently, the algorithm proceeds into using some method to fetch the top-k most similar (according to the label information of e) codes from C. Although our implementation uses a particular choice for this step, we kept the algorithm general and use two function sim and f (line 5) that are general enough to capture most approaches possible for implementing this step. In the case that string similarity algorithms are used, f(·) is the identity function and sim is some string metric like the Levenstein distance. In case sentence embeddings are used, f is a function that maps the label of each entity to some vector and sim is the similarity between those vectors (cosine similarity or angular-distance based). Using the score between the label of input entity e with the labels of the coding system entities, the top-k ranked codes are kept (line 6).

Using this set of top-k codes, it is possible to score the codes returned by function getCodes. Every code returned by this function receives a maximum score of 1 which is penalised with the minimum distance of that code with the codes returned by the similarity-based retrieval approach. Distance is measured with respect to the hierarchy and graph induced by C. If some code c ∈ getCodes(e; C) also appears in embCodes, then the distance between these two codes is 0 and c will receive the maximum score 1. If the code is a child or parent, then the score will be 0 while if one considers longer paths in the hierarchy of C (e.g., siblings or descendants/ancestors), then the score would be even lower (negative).

Algorithm 2

Algorithm 2 concept2code$_k$ (e, $\mathcal{C}$, k, thr)

Input: an entity e from the KB, a coding system $\mathcal{C}$ that we want to translate e, a positive integer κ and a threshold thr.
1: S = get Codes(e, $\mathcal{C}$)
2: if |S| == 1 then -continued Algorithm 2

3:     return {⟨c, 1⟩ | c ∈ S}
4: end if
5: allCds := {⟨c, sim(f(c,ℓ),f(e, ℓ))⟩ | c ∈ $\mathcal{C}$ }
6: embCodes := π1 (top(k, allCds))
7: OrderedSet := { }
8: for c ∈ S do
9:     score := 1 − min$_{c' \in embCodes}$ distance$_\mathcal{C}$(c, c')
10:    if score ≥ thr then
11:        OrderedSet : = OrderedSet ∪ {⟨c, score⟩}
12:    end if
13: end for
14: return OrderedSet In other words, according to a further embodiment, it is possible to link the third and first knowledge bases 48, 44 (coding systems) via the second knowledge base 13. This embodiment relates to the description above in relation to algorithm 2. In this embodiment, the second knowledge base 13 acts as a central hub through which all links are established. This approach facilitates interoperability of the first and third knowledge bases 44, 48. Beneficially, linking the first and third knowledge bases (coding systems) 44, 48, via the second knowledge base 13, means that mappings between entities of the respective first and third knowledge bases 44, 48, are not required and the mappings to and from the second knowledge base 13 can be used exclusively. This approach reduces the number of mappings required when using the second knowledge base 13 as a central hub. The reduced number of mappings reduces the memory required.

Figure 9:
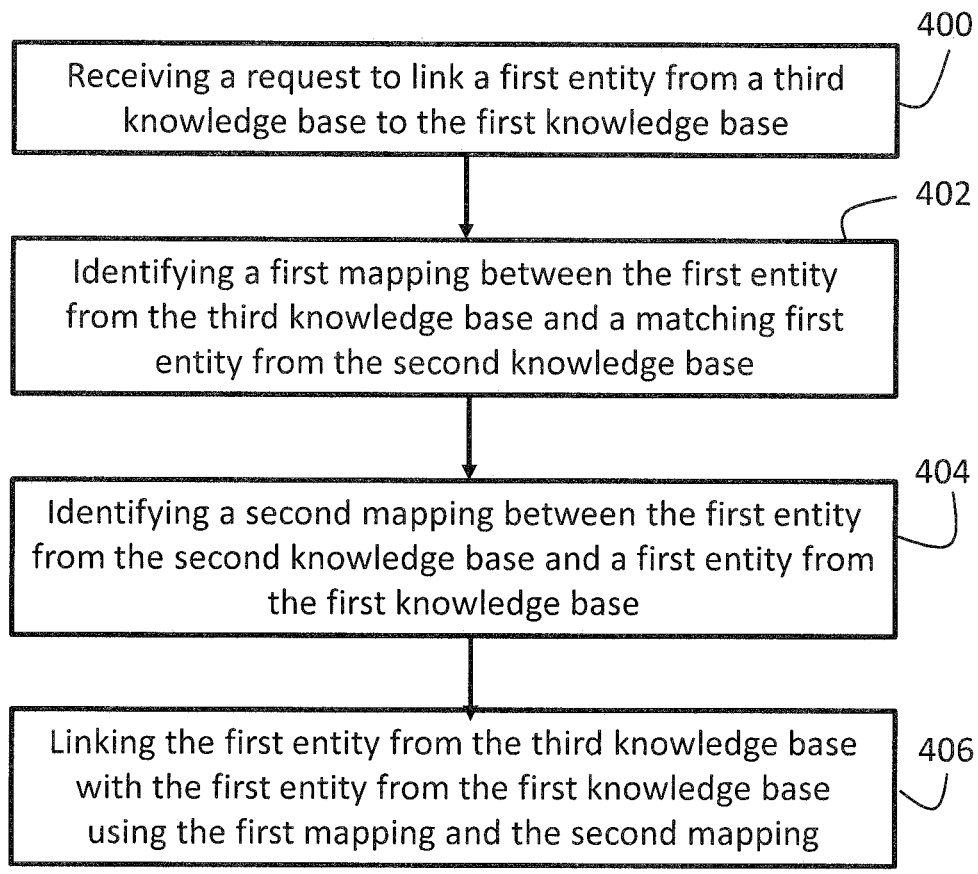
FIG. 9 shows an embodiment of a method of connecting a third knowledge base to a first knowledge base via a central, second knowledge base.

With reference to FIG. 9, this further embodiment includes receiving a request to link a first entity (c6) from a third knowledge base 48 to the first knowledge base 44 at step 400. Next, at step 402, a first mapping is identified between the first entity (c6) from the third knowledge base 48 and a matching first entity (e5) from the second knowledge base 13. Next, at step 404, a second mapping is identified between the first entity (e5) from the second knowledge base 13 and a first entity (c3) from the first knowledge base 44. Finally, at step 406, the first entity (c6) from the third knowledge base 48 is linked with the first entity (c3) from the first knowledge base 44 using the first mapping and the second mapping.

It is noted here that the second mapping is a partial mapping between the first entity (e5) of the second knowledge base 13 and the first entity (c3) of the first knowledge base 44. The term "partial mapping" is not a direct mapping, and is used to define an indirect mapping via a related node of the hierarchy. Step 404 may be expanded on in more detail.

Figure 10:
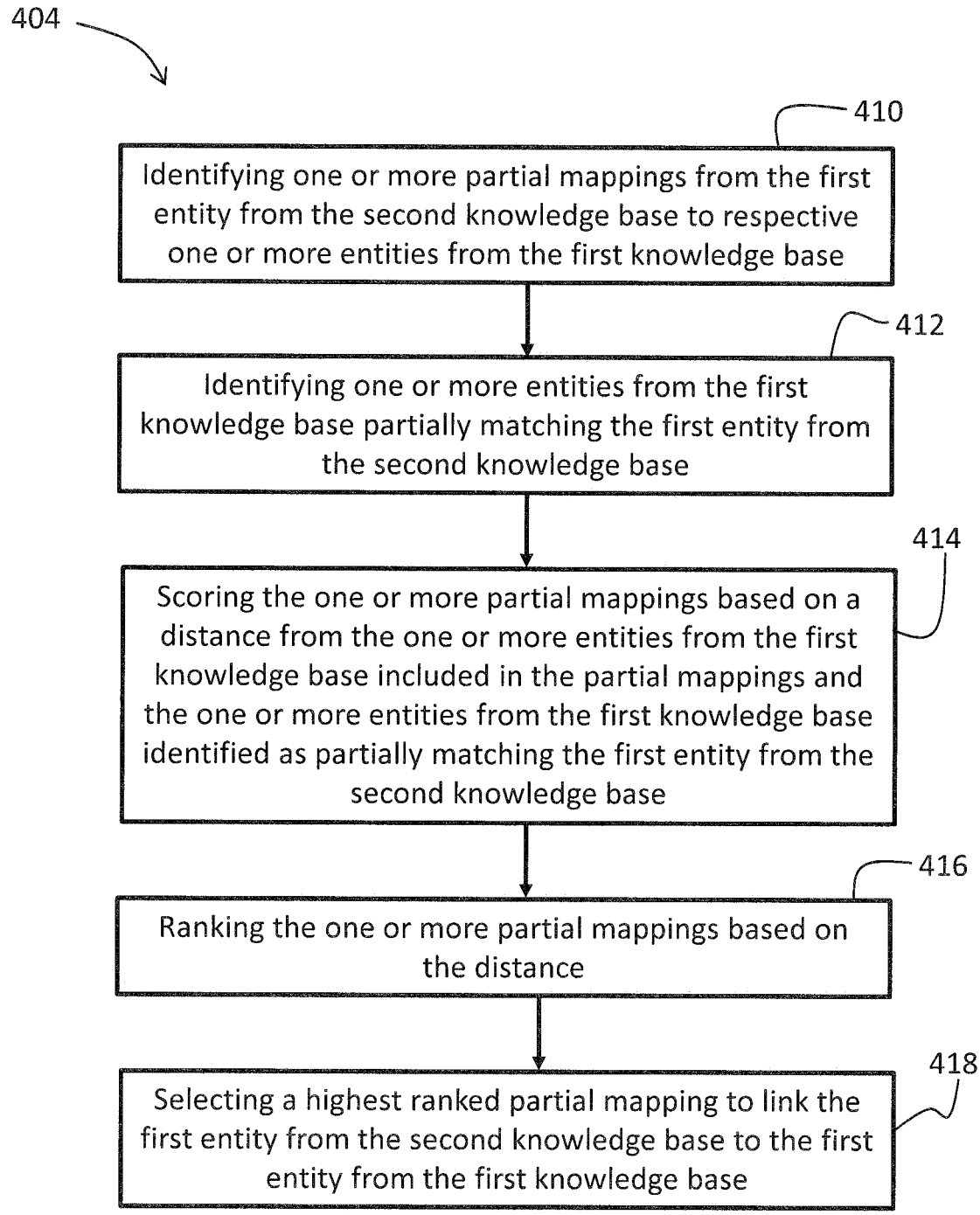
FIG. 10 shows a method of identifying a second mapping between the first entity from the second knowledge base and a first entity from the first knowledge base according to the method outlined in FIG. 9.

Lines 1-4 of algorithm 2 provide a function for retrieving a one-to-one mapping between the first entity of the second knowledge base 13 and the first entity of the first knowledge base 44. In the event that a one-to-one mapping is not found, the algorithm proceeds to lines 5-14, which may be described alternatively with respect to FIGS. 10 and 11.

At step 410, one or more partial mappings is defined from the first entity (e5) from the second knowledge base 13 to respective one or more entities from the first knowledge base 44. At step 412, the one or more entities is identified from the first knowledge base 44 that partially match the first entity (e5) from the second knowledge base 13. The one or more entities from the first knowledge base 44 may be identified by a search of the labels of the plurality of entities from the first knowledge base 44. Next, at step 414, the one or more partial mappings are scored based on a distance from the one or more entities from the first knowledge base 44 included in the partial mappings and the one or more entities from the first knowledge base 44 identified as partially matching the first entity (e5) from the second knowledge base 13. The distance may relate to the number of hops between entities in the first knowledge base 44 that are required in order to link the entity from the partial mapping with an entity identified by the search.

At step 416, the one or more partial mappings may be ranked based on the distance. At step 418, a highest ranked partial mapping is selected to link the first entity (e5) from the second knowledge base 13 to the first entity (c3) from the first knowledge base 44.

Figure 11:
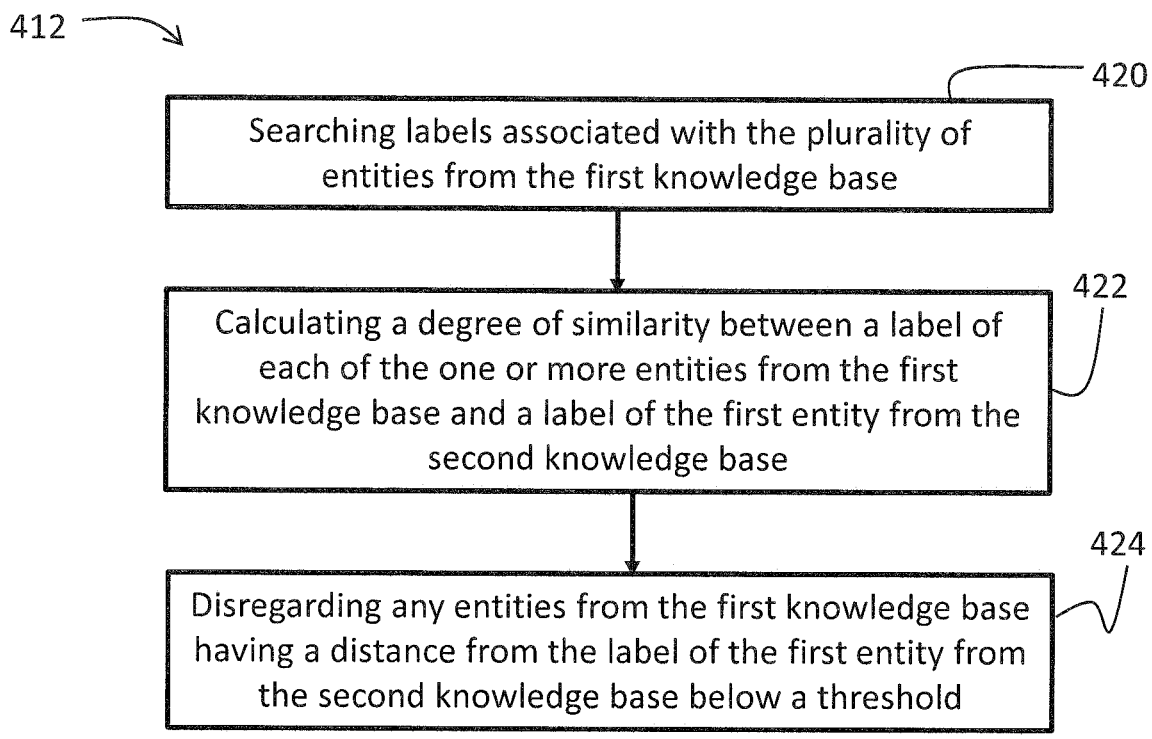
FIG. 11 shows a method of identifying one or more entities from the first knowledge base partially matching the first entity from the second knowledge base, according to the method outlined in FIG. 10.

Step 412 is better described with reference to FIG. 11, where step 420 relates to searching labels associated with the plurality of entities from the first knowledge base. Next at step 422, a degree of similarity is calculated between a label of each of the one or more entities from the first knowledge base 44 and a label of the first entity (e5) from the second knowledge base 13. Next, at step 424, any entities from the first knowledge base 44 having a distance from the label of the first entity (e5) from the second knowledge base 13 are disregarded if they are below a threshold.

It will be appreciated that the foregoing detail described is provided to illustrate the inventive concepts described herein, and that the embodiments described herein should not be interpreted as limiting. The scope of the present disclosure is provided in the claims.

The subject-matter of the present disclosure is best described with reference to the following numbered clauses.

Clause 1. A computer-implemented method of enabling interoperability between a first knowledge base and a second knowledge base,
  wherein each knowledge base is graphically represented and includes a plurality of nodes each defining a concept and a plurality of relations linking the plurality of nodes,
  wherein the first knowledge base and the second knowledge base are encoded using different coding standards, the method comprising:
    identifying an entity from the plurality of entities in the second knowledge base;
    obtaining a mapping between the identified entity from the second knowledge base and a matching entity from the first knowledge base; and
    creating and storing a link between the identified entity from the second knowledge base and the matching entity from the first knowledge base.

Clause 2. The computer-implemented method of clause 1, wherein the entities in the first and second knowledge bases each include a label, and wherein identifying the entity from the first knowledge base includes searching the first knowledge base for a predetermined label.

Clause 3. The computer-implemented method of clause 1, further comprising sending the link to a user for verification.

Clause 4. A computer-implemented method of enabling interoperability between a first knowledge base and a second knowledge base,
  wherein each knowledge base is graphically represented and includes a plurality of nodes each defining a concept and a plurality of relations linking the plurality of nodes,
  wherein the first knowledge base and the second knowledge base are encoded using different coding standards, the method comprising:
    identifying a first entity in the second knowledge base;
    identifying a first entity in the first knowledge base that partially matches the first entity in the second knowledge base;
    adding a second entity to the second knowledge base that matches the first entity from the first knowledge base, and a third entity to the second knowledge base that matches the second entity from the first knowledge base;
    generating and storing a link between the second entity from the second knowledge base and the first entity from the first knowledge base, and a link between the third entity from the second knowledge base and the second entity from the first knowledge base; and
    generating and storing a relation between the first entity from the second knowledge base and the second entity from the second knowledge base, and between the first entity from the second knowledge base and the third entity from the second knowledge base.

Clause 5. The computer-implemented method of clause 4, wherein the entities in the first and second knowledge bases each include a label, and wherein identifying the first entity from the first knowledge base includes searching the first knowledge base for one or more labels at least partially matching a label of the first entity from the second knowledge base.

Clause 6. The computer-implemented method of clause 5, wherein searching includes a key word search.

Clause 7. The computer-implemented method of clause 4, further comprising sending the link to a user for verification.

Clause 8. A computer-implemented method of enabling interoperability between a first knowledge base and a second knowledge base,
  wherein each knowledge base is graphically represented and includes a plurality of nodes each defining a concept and a plurality of relations linking the plurality of nodes,
  wherein the first knowledge base and the second knowledge base are encoded using different coding standards, the method comprising:
    identifying a first entity in the first knowledge base;
    identifying first and second entities in the second knowledge base that at least partially match the first entity from the first knowledge base; and
    selecting a closest match to the first entity from the first knowledge base out of the first and second entities from the second knowledge base; and
    generating and storing a link between the most closely matched first or second entity from the second knowledge base and the first entity from the first knowledge base.

Clause 9. The computer-implemented method of clause 8, further comprising adding a relation between the first and second entities from the second knowledge base.

Clause 10. The computer-implemented method of clause 8, wherein selecting a closest match comprises determining a distance between a vector of each of the first and second entities from the second knowledge base and a vector of the first entity from the first knowledge base; ranking the first and second entities according to the distance; and selecting the closest match as the entity with the closest distance to the first entity.

Clause 11. The computer-implemented method of clause 8, wherein the entities in the first and second knowledge bases include a label, and wherein identifying the first and second entities from the second knowledge base includes searching the second knowledge base for a label at least partially matching a label of the first entity from the first knowledge base.

Clause 12. The computer-implemented method of clause 11, wherein searching includes a key word search.

Clause 13. The computer-implemented method of clause 8, further comprising sending the link to a user for verification.

Clause 14. A computer-implemented method of enabling interoperability between a first knowledge base and a second knowledge base,
  wherein each knowledge base is graphically represented and includes a plurality of nodes each defining a concept and a plurality of relations linking the plurality of nodes,
  wherein the first knowledge base and the second knowledge base are encoded using different coding standards, the method comprising:
  identifying a first entity in the first knowledge base;
  identifying that no entity in the second knowledge base matches the first entity in the first knowledge base;
  identifying a second entity in the first knowledge base, the second entity from the first knowledge base taxonomically linked to the first entity from the first knowledge base, wherein the second entity in the first knowledge base matches a first entity in the second knowledge base;
  adding a second entity to the second knowledge base matching the first entity from the first knowledge base;
  adding a relation between the first and second entities from the second knowledge base; and
  generating and storing a link between the second entity from the second knowledge base and the first entity from the first knowledge base.

Clause 15. The computer-implemented method of clause 14, wherein the entities in the first and second knowledge bases include a label, and wherein identifying that no entity from the second knowledge base matches the first entity from the first knowledge base includes performing a search for a label that matches the first entity from the first knowledge base, and returning no matches.

Clause 16. The computer-implemented method of clause 14, further comprising sending the link to a user for verification.

Clause 17. A computer-implemented method of enabling interoperability between a first knowledge base and a third knowledge base via a second knowledge, the method comprising:
  wherein each of the first, second, and third knowledge bases being graphically represented and including a plurality of nodes each defining a concept and a plurality of relations linking the plurality of nodes,
  wherein each of the first, second, and third knowledge bases are encoded using a different coding standard,
  wherein the method comprises:
  receiving a request to link a first entity from the third knowledge base to the second knowledge base;
  identifying a first mapping between the first entity from the third knowledge base and a matching first entity from the second knowledge base;
  identifying a second mapping between the first entity from the second knowledge base and a first entity in the first knowledge base; and
  linking the first entity from the third knowledge base with the first entity from the second knowledge base using the first mapping and the second mapping.

Clause 18. The computer-implemented method of clause 17, wherein identifying the first mapping includes retrieving a predetermined one-to-one mapping from a database.

Clause 19. The computer-implemented method of clause 17, wherein identifying the second mapping between the first entity from the second knowledge base and the first entity from the first knowledge base includes identifying a one-to-one mapping from a database of predetermined mappings, the one-to-one mapping being from the first entity from the second knowledge base to the first entity from the first knowledge base.

Clause 20. The computer-implemented method of clause 17, wherein identifying the second mapping includes:
  identifying one or more partial mappings from the first entity from the second knowledge base to respective one or more entities from the first knowledge base;
  identifying one or more entities from the first knowledge base partially matching the first entity from the second knowledge base;
  scoring the one or more partial mappings based on a distance from the one or more entities from the first knowledge base included in the partial mappings and the one or more entities from the first knowledge base identified as partially matching the first entity from the second knowledge base;
  ranking the one or more partial mappings based on the distance; and
  selecting a highest ranked partial mapping to link the first entity from the second knowledge base to the first entity from the first knowledge base.

Clause 21. The computer-implemented method of clause 20, wherein identifying the one or more entities in the first knowledge base includes:
  searching labels associated with the plurality of entities from the first knowledge base;
  calculating a degree of similarity between a label of each of the one or more entities from the first knowledge base and a label of the first entity from the second knowledge base; and
  disregarding any entities from the first knowledge base having a distance from the label of the first entity from the second knowledge base below a threshold.

Clause 22. The computer-implemented method of clause 21, wherein calculating the degree of similarity between the label of each of the one or more entities from the first knowledge base and the label of the first entity from the second knowledge base comprises calculating a distance between each label from the first knowledge base and the label of the first entity from the second knowledge base.

Clause 23. The computer-implemented method of clause 22, wherein calculating the degree of similarity comprises identifying a vector associated with each label from the first knowledge base and calculating a distance to a vector associated with a label from the second knowledge base.

Clause 24. The computer-implemented method of clause 20, wherein scoring the one or more partial mappings includes counting a number of hops required from an entity from the first knowledge base included in a partial mapping and each of the one or more identified entities from the first knowledge base, wherein the number of hops is inversely proportional to the score.

Clause 25. A non-transitory computer-readable medium including instructions stored thereon that, when executed by a processor, cause the processor to perform the method of any preceding claim.

The invention claimed is:

1. A computer-implemented method of enabling interoperability between a first knowledge base and a second knowledge base,
wherein each knowledge base is graphically represented and includes a plurality of nodes each defining a concept and a plurality of relations linking the plurality of nodes,
wherein the first knowledge base and the second knowledge base are encoded using different coding standards, the method comprising:
identifying a first node in the second knowledge base;
identifying a first node in the first knowledge base that partially matches the first node in the second knowledge base, wherein identifying a partial match comprises identifying a key word of the first node in the first knowledge base within a key word of the first node in the second knowledge base;
identifying a second node in the first knowledge base that partially matches the first node in the second knowledge base;
adding a second node to the second knowledge base that matches the first node from the first knowledge base, and a third node to the second knowledge base that matches the second node from the first knowledge base;
generating and storing a link between the second node from the second knowledge base and the first node from the first knowledge base, and a link between the third node from the second knowledge base and the second node from the first knowledge base; and
generating and storing a relation between the first node from the second knowledge base and the second node from the second knowledge base, and between the first node from the second knowledge base and the third node from the second knowledge base, wherein:
the nodes in the first and second knowledge bases each include a label,
identifying the first node from the first knowledge base includes searching the first knowledge base for one or more labels having a key word of one or more key words matching a key word of one or more key words of a label of the first node from the second knowledge base,
identifying the second node in the first knowledge base includes searching the first knowledge base for one or more labels having a key word of one or more key words matching a key word of one or more key words of a label of the first node from the second knowledge base,
adding the second node to the second knowledge base comprises adding the second node to the second knowledge base to include a label having an exact linguistic match to the label of the first node from the first knowledge base, and
adding the third node to the second knowledge base comprises adding the third node to the second knowledge base to include a label having an exact linguistic match to the label of the second node from the first knowledge base.

2. The computer-implemented method of claim 1 wherein searching includes a key word search.

3. The computer-implemented method of claim 1, further comprising sending the link to a user for verification.

4. A non-transitory computer-readable medium including instructions stored thereon that, when executed by a processor, cause the processor to perform the method of claim 1.

5. A computer-implemented method of enabling interoperability between a first knowledge base and a second knowledge base,
wherein each knowledge base is graphically represented and includes a plurality of nodes each defining a concept and a plurality of relations linking the plurality of nodes,
wherein the first knowledge base and the second knowledge base are encoded using different coding standards, the method comprising:
identifying a first node in the first knowledge base;
identifying that no node in the second knowledge base matches the first node in the first knowledge base;
identifying a second node in the first knowledge base, the second node from the first knowledge base taxonomically linked to the first node from the first knowledge base, wherein the second node in the first knowledge base matches a first node in the second knowledge base;
adding a second node to the second knowledge base matching the first node from the first knowledge base;
adding a relation between the first and second nodes from the second knowledge base; and
generating and storing a link between the second node from the second knowledge base and the first node from the first knowledge base.

6. The computer-implemented method of claim 5, wherein the nodes in the first and second knowledge bases include a label, and wherein identifying that no node from the second knowledge base matches the first node from the first knowledge base includes performing a search for a label that matches the first node from the first knowledge base, and returning no matches.

7. The computer-implemented method of claim 5, further comprising sending the link to a user for verification.

8. A non-transitory computer-readable medium including instructions stored thereon that, when executed by a processor, cause the processor to perform the method of claim 5.

* * * * *